(12) United States Patent
Chen et al.

(10) Patent No.: US 7,396,799 B2
(45) Date of Patent: *Jul. 8, 2008

(54) HIGHLY ACTIVE SLURRY CATALYST COMPOSITION

(75) Inventors: Kaidong Chen, Albany, CA (US); Bruce E. Reynolds, Martinez, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/627,593

(22) Filed: Jan. 26, 2007

(65) Prior Publication Data

US 2007/0179055 A1    Aug. 2, 2007

Related U.S. Application Data

(63) Continuation-in-part of application No. 10/938,003, filed on Sep. 10, 2004, now abandoned.

(51) Int. Cl.
*B01J 27/04* (2006.01)
*B01J 27/047* (2006.01)
*B01J 27/051* (2006.01)

(52) U.S. Cl. .......................... 502/216; 502/3; 502/159; 502/219; 502/220; 502/221; 502/222; 502/223

(58) Field of Classification Search .................. 502/3, 502/159, 216, 219, 220, 221, 222, 223
See application file for complete search history.

(56) References Cited

U.S. PATENT DOCUMENTS 5,164,075 A * 11/1992 Lopez .......................... 208/215
5,484,755 A * 1/1996 Lopez .......................... 502/219

* cited by examiner

*Primary Examiner*—Elizabeth D Wood
(74) *Attorney, Agent, or Firm*—Penny L. Prater

(57) ABSTRACT

The instant invention is directed to the preparation of a slurry catalyst composition. The slurry catalyst composition is prepared in a series of steps, involving mixing a Group VIB metal oxide, particularly molybdenum and aqueous ammonia to form an aqueous mixture and sulfiding the mixture to form a slurry. The slurry is then promoted with a Group VIII metal. Subsequent steps involve mixing the slurry with a hydrocarbon oil, and combining the resulting mixture with hydrogen gas (under conditions which maintain the water in a liquid phase) to produce the active slurry catalyst.

16 Claims, 1 Drawing Sheet

HIGHLY ACTIVE SLURRY CATALYST COMPOSITION

This application is a continuation-in-part of application Ser. No. 10/938003, filed Sep. 10, 2004 now abandoned, and claims priority therefrom.

FIELD OF THE INVENTION

The present invention relates to the preparation of slurry catalyst compositions useful in the processing of heavy oils. These oils are characterized by low hydrogen to carbon ratios and high carbon residues, asphaltenes, nitrogen, sulfur and metal contents.

BACKGROUND OF THE INVENTION

Slurry catalyst compositions and means for their preparation are known in the refining arts. Some examples are discussed below.

U.S. Pat. No. 4,710,486 discloses a process for the preparation of a dispersed Group VIB metal sulfide hydrocarbon oil hydroprocessing catalyst. Process steps include reacting aqueous ammonia and a Group VIB metal compound, such as molybdenum oxide or tungsten oxide, to form a water soluble oxygen-containing compound such as ammonium molybdate or tungstate.

U.S. Pat. No. 4,970,190 discloses a process for the preparation of a dispersed Group VIB metal sulfide catalyst for use in hydrocarbon oil hydroprocessing, This catalyst is promoted with a Group VIII metal. Process steps include dissolving a Group VIB metal compound, such as molybdenum oxide or tungsten oxide, with ammonia to form a water soluble compound such as aqueous ammonium molybdate or ammonium tungstate.

U.S. Pat. Nos. 5,164,075 and 5,484,755 (the latter patent being incorporated by reference) disclose processes for preparation of high activity slurry catalysts for hydroprocessing heavy hydrocarbon oils produced from Group VIB metal compounds. An aqueous mixture of the metal compound is sulfided with from greater than about 8 to about 14 standard cubic feet of hydrogen sulfide per pound of Group VIB metal. These patents demonstrate a process of forming a slurry catalyst precursor and adding it to a heavy feed oil to form the active catalyst. These patents do not, however, demonstrate the criticality of the oil viscosity in the formation of a highly active catalyst composition, nor the significance of maintaining water in the liquid phase in a crucial reaction step.

In the inventions disclosed in U.S. Pat. Nos. 5,164,075 and 5,484,755, the failure to form the oil and water emulsion or the slurry phase results in an inactive catalyst or a catalyst having low activity.

This application discloses a new slurry catalyst composition that is highly active. This activity results from preparation of the catalyst using a process employing a single hydrocarbon oil (preferably a vacuum gas oil) having an appropriate viscosity range at 212° F.

SUMMARY OF THE INVENTION

This invention is directed to a highly active catalyst composition which is suitable for processing heavy hydrocarbon oils. The catalyst is prepared by the following steps, resulting in a catalyst composition suitable for the hydroconversion of heavy oils, which is prepared by:

A catalyst composition suitable for the hydroconversion of heavy oils, which is prepared by:

(a) mixing molybdenum oxide and aqueous ammonia to form a molybdenum mixture;
(b) sulfiding, in a first reaction zone, the aqueous mixture of step (a) with a gas comprising hydrogen sulfide to a dosage greater than 8 SCF of hydrogen sulfide per pound of molybdenum to form a slurry;
(c) promoting the slurry with a Group VIII metal compound;
(d) mixing the slurry of step (c) with hydrocarbon oil having a viscosity of at least 2 cSt @ 212° F. but less than about 15 cSt @ 212° F. at a speed in the range from 100 to 1600 RPM to form and maintain a homogenous slurry designated as Mixture X;
(e) combining Mixture X with hydrogen gas in a second reaction zone, under conditions which maintain the water in Mixture X in a liquid phase, and mixing at a speed in the range from 100 to 1600 RPM in order to maintain as homogenous slurry thereby forming an active catalyst composition admixed with a liquid hydrocarbon; and
(f) recovering the active catalyst composition.

This new highly active slurry catalyst composition may be stored in an active and concentrated state. The catalyst composition can be directly introduced into any of the known heavy oil or residuum upgrading processes under the existing conditions of that process. The catalyst can upgrade the very high viscosity carbonaceous and/or highly paraffinic feedstocks with or without dilution of the feedstock.

BRIEF DESCRIPTION OF THE DRAWING

The FIGURE illustrates the steps involved in the preparation of the catalyst composition.

DETAILED DESCRIPTION OF THE INVENTION

Figure 1:
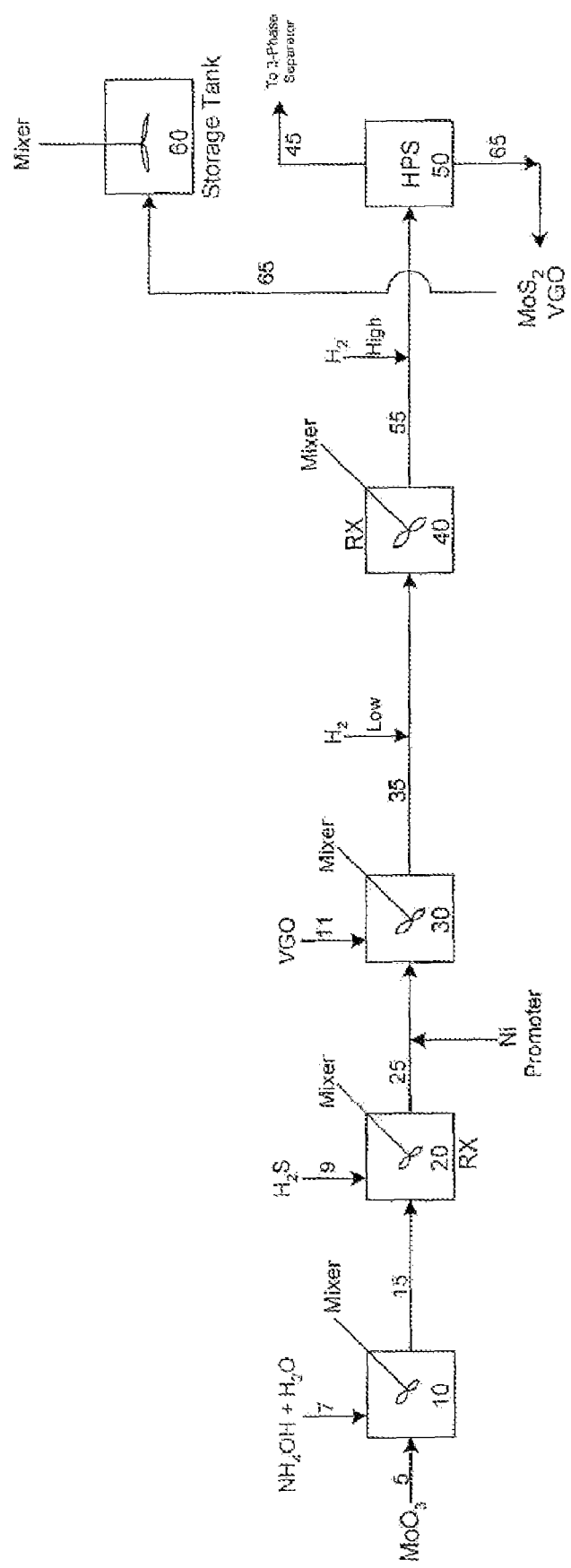

This invention relates to a new highly active slurry catalyst composition formed from the combination of a slurry comprising the Group VIB metal molybdenum and Group VIII metals as well as a hydrocarbon oil having a viscosity of at least 2 cSt (or 32.8 SSU) @ 212° F. The preferred viscosity range for the hydrocarbon oil is from at least about 2 cSt (or 32.8 SSU) @ 212° F. to 15 cSt (or 77.9 SSU) @ 212° F.

The FIGURE illustrates the steps involved in the process of this invention. The active slurry catalyst composition is prepared by mixing line 5, containing an oxide of molybdenum, and line 7, containing aqueous ammonia, in a mixing zone 10. The temperature of the mixing zone is generally in the range from about 80° F. to about 200° F., preferably from about 100° F. to about 150° F., and most preferably from about 110° F to about 120° F. The pressure of the mixing zone 10 is generally from about atmospheric pressure to about 100 psig, preferably from about 5 psig to about 35 psig, and most preferably from about 10 psig to about 35 psig. The molybdenum oxide is dissolved in water containing the ammonia. The amount of ammonia added is based on the ratio of $NH_3$ to molybdenum oxide in lbs/lbs and generally ranges from 0.1 lbs/lbs to about 1.0 lbs/lbs, preferably from about 0.15 lbs/lbs to about 0.50 lbs/lbs, and most preferably from about 0.2 lbs/lbs to about 0.30 lbs/lbs. The dissolved molybdenum oxide in aqueous ammonia is moved via line 15 to the first reaction zone.

The amount of hydrogen sulfide (line 9) added to the reaction zone 20 is based on the ratio of $H_2S$ to molybdenum oxide in SCF/lbs and generally ranges from 4.0 SCF/lbs to about 20 SCF/lbs, preferably from about 8.0 SCF/lbs to about 18 SCF/lbs, and most preferably from about 12 to 14 SCF/lbs. The reaction time in the first reaction zone ranges from about 1 hour to 10 hours, preferably from 3 hours to 8 hours, and most preferably from about 4 hours to 6 hour per pound of molybdenum oxide, Conditions include a temperature in the range from 80° F. to 200° F., preferably in the range from 100° F. to 180° F., and most preferably in the range from 130° F. to 160° F. Pressure is in the range from 100 to 3000 psig, preferably in the range from 200 to 1000 psig, and most preferably from 300 to 500 psig. The resultant slurry is the catalyst precursor in an aqueous slurry phase.

The resultant slurry is combined with a Group VIII metal compound such as Ni or Co, as disclosed in U.S. Pat. No. 5,484,755. As an enhancement of the denitrogenation activity of the active slurry catalyst of the present invention, it is preferred that a Group VIII metal compound be added to the slurry before mixing the slurry with feed oil and a hydrogen containing gas at elevated temperature and pressure. Such Group VIII metals are exemplified by nickel and cobalt. It is preferred that the weight ratio of nickel or cobalt to molybdenum range from about 1:100 to about 1:2. It is most preferred that the weight ratio of nickel to molybdenum range from about 1:25 to 1:10, i.e., promoter/molybdenum of 4-10 weight percent. The Group VIII metal, exemplified by nickel, is normally added in the form of the sulfate, and preferably added to the slurry after sulfiding at a pH of about 10 or below and preferably at a pH of about 8 or below. Group VIII metal nitrates, carbonates or other compounds may also be used. In view of the high activity of the slurry catalyst of the present invention, the further promotion by Group VIII metal compounds is very advantageous.

The slurry containing the Group VIII metal promoter is moved, via line 25, to mixing zone 30. Mixing zone 30 employs an inert atmosphere which can comprise nitrogen, refinery gas, or any other gas having little or no oxygen. The slurry and a hydrocarbon oil (line 11), such as VGO, are mixed continuously in a high shear mode to maintain a homogeneous slurry in mixer 30. High shear mixing is defined as intense mixing wherein solids are suspended completely off the vessel bottom and slurry is supplied to at least one third of the fluid batch height and is suitable for slurry draw off at low exit nozzle elevators. High shear mixing encompasses a range from 100 to 1600 RPM. Preferably the mixing rate is greater than 500 RPM and most preferably greater than 1500 RPM.

The hydrocarbon oil has a kinetic viscosity of at least, 2 cSt (32.8 SSU) @ 212° F. The kinetic viscosity can generally range from about 2 cSt (32.8 SSU) @ 212° F. to about 15 cSt (77.9 SSU) @ 212° F., preferably from about 4 cSt (39.5 SSU) @ 212° F. to about 10 cSt (59.2 SSU) @ 212° F., and most preferably from about 5 cSt (42.7 SSU) @ 212° F. to about 8 cSt (52.4 SSU) @ 212° F. The hydrocarbon oil causes the initial transformation of the, catalyst precursor to an oil base from a water base. The ratio of molybdenum to oil is at least less than 1.0, preferably less than 0.5, and more preferably less than 0.1. If the kinetic viscosity of the oil is below about 2 cSt (32.8 SSU) @ 212° F. or above about 15 cSt (77.9 SSU) @ 212° F., the first transformation of the catalyst precursor will result in catalyst particles agglomerating or otherwise not mixing. This mixture is known in the claims as Mixture X.

The material from mixing zone 30 (Mixture X) moves to reaction zone 40 via line 35. Hydrogen is continuously added to the mixture reaction zone 40, and high shear mixing is employed in the reaction zone 40 in order to maintain a homogenous slurry. Hydrogen is added at low pressure prior to reactor 40 and at high pressure following reactor 40. This is done in order to keep water in liquid phase in reactor 40, change water to vapor phase after reactor 40 in order to flash off the water. When the low H2 rate is used in reactor 40, water is still in liquid phase. Following reactor 40, more H2 is added, so the water changes to vapor phase permitting separation from oil slurry in high pressure separator. The process conditions of reactor 40 are critical to forming the final catalyst. The water in the mixture must be maintained in a liquid phase.

The temperature of the reaction zone 40 generally ranges from about 300° F. to 600° F., preferably from about 350° F. to about 500° F., and most preferably from about 350° F. to about 450° F. The pressure of the reaction zone 40 generally ranges from about 100 psig to about 3000 psig, preferably from about 200 psig to about 1000 psig, and most preferably from about 300 psig to about 500 psig The hydrogen flow to the reaction zone 40 generally ranges from about 300 SCFB to about 2000 SCFB, preferably from about 300 SCFB to about 1000 SCFB, and most preferably from about 300 SCFB to about 500 SCFB The reaction time in the reaction zone 40 ranges from about 10 minutes to 5 hours, preferably from 30 minutes to 3 hours, and most preferably from about 1 hour to 1.5 hours The resultant slurry mixture is the active catalyst composition in admixture with the hydrocarbon oil.

The slurry mixture is passed, through line 55, to high pressure separator 50. More hydrogen is added in line 55 so the water changes to vapor phase. It can then be separated from oil slurry in the high pressure separator. The high pressure separator operates in a range from 300° F. to 700° F. Gases and water are removed overhead through line 45 and passed to a three phase separator. The active catalyst composition is moved through line 65 to storage tank 60. The active catalyst composition is continuously mixed in storage tank 60 to maintain a homogenous slurry in a hydrogen atmosphere with little or no oxygen. In this way, the catalyst activity and stability are maintained.

The catalyst composition is useful for upgrading carbonaceous feedstocks which include atmospheric gas oils, vacuum gas oils, deasphalted oils, olefins, oils derived from tar sands or bitumen, oils derived from coal, heavy crude oils, synthetic oils from Fischer-Tropsch processes, and oils derived from recycled oil wastes and polymers. The catalyst composition is useful for but not limited to hydrogenation upgrading processes such as thermal hydrocracking, hydrotreating, hydrodesulphurization, hydrodenitrification, and hydrodemetallization.

EXAMPLES

Example Catalyst Preparation 540 gram $MoO_3$ is mixed with 79 gram of $NH_3$ and 2381 gram of $H_2O$ to form a solution of total 3000 gram. The solution is then reacted with 10.71 SCF of $H_2S$ by passing a gas mixture of 20% $H_2S$ in $H_2$ into the solution under strong mixing. The reactor temperature is 150° F. and the total pressure is 400 psig and the reaction time is 4 hours. After reaction, 460 gram $NiSO_4$ solution which contains 36 gram of Ni is added to the above obtained slurry. The obtained slurry mixture is then mixed with 8000 gram of vacuum gas oil at 100° F. The viscosity of the VGO is 5 cSt @ 212° F. The resulting mixture is then pumped into a continuously flow tanked reactor (perfectly mixed flow reactor) with $H_2$. The $H_2$ gas rate is 300 SCF/B. The reactor pressure is 400 psig and reactor temperature is 400° F., the total reaction time is 1 hour. The reaction products are mixed with more $H_2$ at a gas rate of 1500 SCF/B and then go to a hot high pressure separator, which is also maintained at a pressure of 400 psig with temperature 500° F. to separate gas and liquid slurry. The obtained liquid slurry contains the highly active catalyst component.

What is claimed is:

1. A catalyst composition suitable for the hydroconversion of heavy oils, which is prepared by:
   (a) mixing molybdenum oxide and aqueous ammonia to form a molybdenum mixture;
   (b) sulfiding, in a first reaction zone, the aqueous mixture of step (a) with a gas comprising hydrogen sulfide to a dosage greater than 8 SCF of hydrogen sulfide per pound of molybdenum to form a slurry;
   (c) promoting the slurry with a Group VIII metal compound;
   (d) mixing the slurry of step (c) with hydrocarbon oil having a viscosity of at least 2 cSt @ 212° F. but less than about 15 cSt @ 212° F. at in the range from 100 to 1600 RPM to form and maintain a homogenous slurry designated as Mixture X;
   (e) combining Mixture X with hydrogen gas in a second reaction zone, under conditions which maintain the water in Mixture X in a liquid phase, and mixing at a speed in the range from 100 to 1600 RPM in order to maintain as homogenous slurry thereby forming an active catalyst composition admixed with a liquid hydrocarbon; and
   (f) recovering the active catalyst composition.

2. The catalyst composition of claim 1, wherein conditions in the first reaction zone comprise a temperature in the range from at least about 80° F. to about 200° F., and a pressure in the range from at least about 100 psig to about 3000 psig.

3. The catalyst, composition of claim 2, wherein conditions in the first reaction zone comprise a temperature in the range from at least about 100° F. to about 180° F., and a pressure in the range from at least about 200 psig to about 1000 psig.

4. The catalyst composition of claim 3, wherein conditions in the first reaction zone comprise a temperature in the range from at least about 130° F. to about 160° F. and a pressure in the range from at least about 300 psig to about 500 psig.

5. The catalyst composition of claim 1, wherein the hydrocarbon oil viscosity ranges from at least about 2 cSt @ 212° F. to about 15 cSt @ 212° F.

6. The catalyst composition of claim 1, wherein the: Group VIII metal compound of step (c) is selected from the group consisting of nickel sulfates and cobalt sulfates.

7. The catalyst composition of claim 6, in which the weight ratio of nickel or cobalt to molybdenum ranges from 1:100 to about 1:2.

8. The catalyst composition of claim 1, wherein the ratio of molybdenum to oil is less than 1.0.

9. The catalyst composition of claim 1, wherein the hydrocarbon oil is a vacuum gas oil.

10. The catalyst composition of claim 1, wherein the conditions of the second reaction zone comprise a temperature in the range from at least about 350° F. to about 600° F. and a pressure in the range from at least about 100 psig to about 3000 psig.

11. The catalyst composition of claim 10, wherein the conditions of the second reaction zone comprise a temperature in the range from at least about 350° F. to about 600° F. and the pressure in the range from at least about 200 psig to about 1000 psig.

12. The catalyst composition of claim 1, which is recovered by means of a high pressure separator.

13. The catalyst composition of claim 1, which exist in an active and concentrated state.

14. The catalyst of claim 12, which is continuously mixed in a storage tank to maintain a homogenous slurry.

15. The catalyst composition of claim 8, wherein the ratio of molybdenum to oil is less than 0.5.

16. The catalyst composition of claim 15, wherein the ratio of molybdenum to oil is less than 0.1.

* * * * *